(12) United States Patent
Fan et al.

(10) Patent No.: US 9,446,999 B2
(45) Date of Patent: Sep. 20, 2016

(54) PROCESS FOR SEPARATING BY ABSORPTION THE PYROLYSIS GAS FROM PREPARATION OF LOWER CARBON OLEFINS

(75) Inventors: Fengtang Fan, Heilongjiang (CN); Xiaobo Wei, Beijing (CN); Longwu Cheng, Heilongjiang (CN); Yingxin Wu, Heilongjiang (CN); Xiangqian Huang, Heilongjiang (CN)

(73) Assignees: FUDE (BEIJING) CHEMICAL & INDUSTRY CO., LTD., Beijing (CN); DAQING PETROCHEMICAL ENGINEERING CO., LTD., Heilongjiang (CN)

( * ) Notice: Subject to any disclaimer, the term of this patent is extended or adjusted under 35 U.S.C. 154(b) by 326 days.

(21) Appl. No.: 14/239,932

(22) PCT Filed: May 31, 2012

(86) PCT No.: PCT/CN2012/076312
§ 371 (c)(1),
(2), (4) Date: Feb. 20, 2014

(87) PCT Pub. No.: WO2013/029401
PCT Pub. Date: Mar. 7, 2013

(65) Prior Publication Data
US 2014/0187840 A1    Jul. 3, 2014

(30) Foreign Application Priority Data
Sep. 1, 2011  (CN) .......................... 2011 1 0256262

(51) Int. Cl.
*C07C 7/11* (2006.01)
(52) U.S. Cl.
CPC ....................................... *C07C 7/11* (2013.01)

(58) Field of Classification Search
None
See application file for complete search history.

(56) References Cited

U.S. PATENT DOCUMENTS

| | | | |
|---|---|---|---|
| 6,601,406 B1 | 8/2003 | Deng et al. | |
| 7,714,180 B2 | 5/2010 | Duhon et al. | |

(Continued)

FOREIGN PATENT DOCUMENTS

| | | |
|---|---|---|
| CN | 1665912 A | 9/2005 |
| CN | 101215214 | 7/2008 |

(Continued)

OTHER PUBLICATIONS

Office Action issued Oct. 21, 2015 in Canadian Patent Application No. 2,840,278.

(Continued)

*Primary Examiner* — Tam M Nguyen
(74) *Attorney, Agent, or Firm* — Oblon, McClelland, Maier & Neustadt, L.L.P.

(57) ABSTRACT

The provided is a process for separating by absorption the pyrolysis gas from preparation of lower carbon olefins, wherein a primary absorbent and a secondary absorbent are introduced into the demethanizer to separate by absorption the feedstock of the demethanizer through countercurrent contact therewith at a moderate temperature and pressure, thereby to obtain a top fraction primarily comprising hydrogen and methane and a bottom fraction primarily comprising the absorbents and C2+ fraction, wherein the primary absorbent essentially is a mixed Cn or Cn+ fraction, the secondary absorbent essentially is a Cn' alkane fraction or mixed Cn' or Cn'+ fraction, and wherein n and n' are independently 3, 4 or 5 with the proviso when the secondary absorbent is a mixed fraction, n' is not 3.

21 Claims, 4 Drawing Sheets

(56) References Cited

U.S. PATENT DOCUMENTS

2004/0211703 A1 10/2004 Duhon et al.
2007/0284286 A1 12/2007 Duhon et al.

FOREIGN PATENT DOCUMENTS

| CN | 101445419 | | 6/2009 |
|---|---|---|---|
| CN | 101973831 | A | 2/2011 |
| CN | 102115355 | A | 7/2011 |
| CN | 102503757 | | 6/2012 |

OTHER PUBLICATIONS

Office Action issued Mar. 30, 2015 in Australian Patent Application No. 2012304075.
Extended European Search Report issued Mar. 10, 2015 in Patent Application No. 12827570.8.
Combined Chinese Office Action and Search Report issued Mar. 13, 2014 in Patent Application No. 201110256262.0 (with English translations of categories of cited documents).
International Search Report Issued Sep. 13, 2012 in PCT/CN12/076312 Filed May 31, 2012.
Action issued Jun. 24, 2015, in corresponding Russian Patent Application No. 2014112339 (with English-language Translation).

US 9,446,999 B2

PROCESS FOR SEPARATING BY ABSORPTION THE PYROLYSIS GAS FROM PREPARATION OF LOWER CARBON OLEFINS

FIELD OF THE INVENTION

The present invention relates to the separation and purification of lower carbon olefins such as ethylene and/or propylene, particularly to a process for separating by absorption the pyrolysis gas from preparation of lower carbon olefins such as ethylene and/or propylene.

BACKGROUND OF THE INVENTION

As important basic petrochemical feedstock, lower carbon olefins such as ethylene and/or propylene have attracted a lot of attention from research and development teams to their preparation as well as subsequent separation and purification. In the past lower carbon olefins such as ethylene and/or propylene were primarily prepared by pyrolysis of petroleum hydrocarbon fractions such as naphtha and light diesel, however, in recent years a process for preparing olefins by pyrolysis of oxygenates had been developed due to the gradual short supply of crude oil.

No matter the pyrolysis is of petroleum hydrocarbons or of oxygenates, the resultant pyrolysis gas is always a mixture of complicated ingredients and depending on the process conditions generally comprises lower carbon olefins such as C2-C4 olefins at relative large amounts, also some non-olefin byproducts such as hydrogen, C1-C6 alkanes and little alkyne as well as in the case of pyrolysis of oxygenates some unreacted oxygenates such as alcohol and/or ether etc. Thus, a complicated separation and purification process is necessary to separate and purify such a complicated pyrolysis gas to obtain lower carbon olefins such as ethylene and/or propylene of polymerization grade.

The pyrolysis gas from preparation of lower carbon olefins is generally subjected to a cryogenic separation process, which typically covers three separation schemes, i.e. sequential scheme removing methane firstly, front end deethanizer scheme removing C2 and the lower fractions firstly, and front end depropanizer scheme removing C3 and the lower fractions firstly. In these separation schemes, the pyrolysis gas is generally pretreated, e.g. cooled, compressed, removed of impurities and dried as well as optionally finished, and then further treated to obtain lower carbon olefins of polymerization grade finally. In these separation schemes, when separating methane and hydrogen from C2+ fractions, a cryogenic separation process with high investment cost and energy consumption is necessary. In order to overcome the disadvantages of the cryogenic separation process, newly proposed is a process for separating by absorption the pyrolysis gas from preparation of lower carbon olefins, i.e. separating methane and hydrogen by absorbing C2+ fractions with an absorbent at moderate temperature and pressure.

In the absorption process, mixed hydrocarbons or pure hydrocarbon are generally used as the absorbents to separate methane and hydrogen from C2+ fractions at reasonable operating conditions and minimize the loss of targeted products such as ethylene and/or propylene as possible as can. In order to minimize the concentration of targeted products such as ethylene and/or propylene at the overhead of the absorption column, some measures such as circulating a lot of absorbent or decreasing the temperature of the absorbent are used to increase the absorption capacity, however, all these measures are with high energy consumptions. Thus, a compromise is necessary between minimizing the loss of targeted products such as ethylene and/or propylene and the energy consumption during the process.

Thus, in the art it is still needed to further improve the yield of targeted products such as ethylene and/or propylene and decrease the energy consumption during the separation and purification of the pyrolysis gas from preparation of lower carbon olefins.

SUMMARY OF THE INVENTION

Based on the composition of the pyrolysis gas from preparation of lower carbon olefins, the present invention further improve the separation of the pyrolysis gas, wherein composite absorbents are used in the demethanizer to separate methane and hydrogen from C2+ fractions, specifically, a mixed hydrocarbon fraction is used as a primary absorbent and a pure hydrocarbon or mixed hydrocarbon fraction is used as a secondary absorbent, so that to obtain lower carbon olefins such as ethylene and/or propylene of polymerization grade with significantly reduced cooling capacity.

Specifically, the present invention provides a process for separating by absorption the pyrolysis gas from preparation of lower carbon olefins, wherein a primary absorbent and a secondary absorbent are introduced into the demethanizer to separate by absorption the feedstock fed to the demethanizer through countercurrent contact therewith at a moderate temperature and pressure, thereby to obtain a top fraction primarily comprising hydrogen and methane and a bottom fraction primarily comprising the absorbents and C2+ fraction, wherein the primary absorbent essentially is a mixed Cn or Cn+ fraction, the secondary absorbent essentially is a Cn' alkane fraction or mixed Cn' or Cn'+ fraction, and wherein n and n' are independently 3, 4 or 5 with the proviso when the secondary absorbent is a mixed fraction, n' is not 3.

According to the process of the present invention, wherein into the demethanizer the feedstock is introduced at the middle or the bottom, the primary absorbent is introduced at the middle, the secondary absorbent is introduced at the top, and in the demethanizer the temperature is above −45□ and the pressure is of 1.5-3.5 MPaG.

According to the process of the present invention, wherein the primary absorbent is preferably introduced into the demethanizer at the middle and the bottom simultaneously with a mass flowrate ratio generally in the range of 1.0-15, preferably in the range of 1.2-10, more preferably in the range of 1.5-8. That is to say, according to the process of the present invention, wherein the primary absorbent may be introduced into the demethanizer at different locations proportionally to absorb C2+ fraction from the lower carbon hydrocarbon mixture gradually, thereby to separate more thoroughly. According to the process of the present invention, wherein the primary absorbent and the feedstock are introduced into the demethanizer at a total mass flowrate ratio in the range of 0.03-4, preferably in the range of 0.05-2.5, more preferably in the range of 0.1-1, and the primary absorbent and the secondary absorbent are introduced into the demethanizer at a total flowrate ratio in the range of 10-1.05, preferably in the range of 8-1.1, more preferably in the range of 6-1.2

According to the process of the present invention, wherein the primary absorbent and the secondary absorbent may be combined in many ways, e.g. the primary absorbent may essentially be mixed C3, C4 or C5 fraction, or may essentially be mixed C3+, C4+ or C5+ fraction, and the secondary absorbent may essentially be C3, C4 or C5 alkane fraction, or may essentially be mixed C4 or C5 fraction, and also may essentially be mixed C4+ or C5+ fraction, wherein the absorbents may be preferably mixed C3 fraction or mixed C3+ fraction and C3 alkane fraction in combination.

Herein, it is noted that "mixed fraction" means the fraction primarily comprises alkanes and olefins with some impurities such as alkynes and cyclic hydrocarbons, e.g. mixed C3 fraction primarily comprises C3 alkane and C3 olefin, and mixed C3+ fraction primarily comprises C3+ alkanes and C3+ olefins, and so on, and "alkane fraction" means the fraction essentially is alkanes with some impurities such as olefins, alkynes and cyclic hydrocarbons, e.g. C3 alkane fraction essentially is C3 alkane, and C3+ alkane fraction essentially is C3+ alkanes, and so on.

Furthermore, both the primary absorbent and the secondary absorbent may be from external sources, however, they are preferably from the pyrolysis gas separation scheme per se, that is to say, both the primary absorbent and the secondary absorbent are preferably supplied by the separation scheme per se. According to the process of the present invention, wherein a specified mixed fraction is used as the primary absorbent in the demethanizer to absorb most of C2+ fraction, then subsequently only the C2+ fraction and the absorbents from the bottom of the demethanizer need to be further separated from each other with less energy consumption; and a specified alkane fraction or mixed fraction is used as the secondary absorbent to be introduced at the top of the demethanizer to further absorb C2+ fraction, so that the top fraction of the demethanizer has a smaller concentration of the targeted olefins such as ethylene and/or propylene; furthermore, it is better that the mixed fraction as the secondary absorbent comprises no or as less as possible of the targeted olefins such as ethylene and/or propylene, so that to further minimize the loss of the targeted olefins due to entrainment or the like; at the same time, the secondary absorbent is used at a relative small amount, thus having little influence to the subsequent separation load.

According to the process of the present invention, the pyrolysis gas from preparation of lower carbon olefins may be separated in various schemes in the art. The pyrolysis gas may be pretreated and optionally finished and then directly fed into the demethanizer, i.e. it is separated in a sequential scheme; or the pyrolysis gas may be pretreated, suitably split and optionally finished and then fed into the demethanizer, i.e. it is separated in a front end depropanizer scheme or front end deethanizer scheme. During the process, C2, C3 and C4 fractions etc. are split out gradually and optionally finished respectively, thereby to obtain the lower carbon olefins such as ethylene and/or propylene of polymerization grade.

Thus, according to the process of the present invention, in addition to demethanizer, the separation process may further comprise compressor, finishing system, deethanizer, depropanizer, debutanizer as well as ethylene distillation column and propylene distillation column etc.

Specifically, according to the process of the present invention, the pyrolysis gas may be separated in a sequential scheme, wherein the pyrolysis gas is compressed and optionally finished and fed into the demethanizer. In such a case, a portion of the mixed C3 fraction derived from the top of the depropanizer may be used as the primary absorbent, and a portion of the C3 alkane fraction derived from the bottom of the propylene distillation column may be used as the secondary absorbent; or a portion of the mixed C3 fraction derived from the top of the depropanizer may be used as the primary absorbent, and a portion of the mixed C4+ fraction derived from the bottom of the depropanizer may be used as the secondary absorbent; or a portion of the mixed C3+ fraction derived from the bottom of the deethanizer may be used as the primary absorbent, and a portion of the mixed C4+ fraction derived from the bottom of the depropanizer may be used as the secondary absorbent; or a portion of the mixed C3+ fraction derived from the bottom of the deethanizer may be used as the primary absorbent, and a portion of the mixed C4 fraction derived from the top of the debutanizer may be used as the secondary absorbent; or a portion of the mixed C4+ fraction derived at the bottom of the depropanizer may be used as the primary absorbent, and a portion of the mixed C4 fraction derived from the top of the debutanizer may be used as the secondary absorbent.

Specifically, according to the process of the present invention, the pyrolysis gas may also be separated in a front end depropanizer scheme, wherein a single depropanizer may be used, or a high pressure depropanizer and a low pressure depropanizer may be used in combination.

When a single depropanizer is used in the front end depropanizer scheme, the pyrolysis gas is compressed and then introduced into the depropanizer, from which the top fraction is optionally finished and then fed into the demethanizer and the bottom fraction is fed into the debutanizer, wherein a portion of the mixed C3 fraction derived from the bottom of the deethanizer may be used as the primary absorbent, and a portion of the C3 alkane fraction derived from the bottom of the propylene distillation column may be used as the secondary absorbent.

When a high pressure depropanizer and a low pressure depropanizer is used in combination in the front end depropanizer scheme, the pyrolysis gas is compressed and then fed into the high pressure depropanizer, from which the top fraction is optionally finished and then fed into the demethanizer and the bottom fraction is fed into the low pressure depropanizer, from which the top fraction is back to the high pressure depropanizer and the bottom fraction is fed into the debutanizer, wherein a portion of the mixed C3 fraction derived from the bottom of the deethanizer may be used as the primary absorbent, and a portion of the C3 alkane fraction derived from the bottom of the propylene distillation column may be used as the secondary absorbent; and herein, a portion or all of the top fraction of the low pressure depropanizer may also be used as the primary absorbent, and in this case from the low pressure depropanizer the remaining portion of the top fraction, if any, is back to the high pressure depropanizer and the bottom fraction is fed into the debutanizer.

Specifically, according to the process of the present invention, the pyrolysis gas may also be separated in a front end deethanizer scheme, which generally comprises two deethanizers, i.e. a first deethanizer and a second deethanizer, wherein the pyrolysis gas is compressed and optionally finished and then fed into the first deethanizer, from which the top fraction is fed into the demethanizer and the bottom fraction is fed into the depropanizer, and the bottom fraction of the demethanizer is fed into the second deethanizer.

More specifically, in the front end deethanizer scheme, a portion of the mixed C3 fraction derived from the top of the depropanizer may be used as the primary absorbent, and a portion of the C3 alkane fraction derived from the bottom of the propylene distillation column may be used as the secondary absorbent; or a portion of the mixed C3+ fraction derived from the bottom of the first deethanizer may be used as the primary absorbent, and a portion of the mixed C4 fraction derived from the top of the debutanizer may be used as the secondary absorbent; or a portion of the mixed C3+ fraction derived from the bottom of the first deethanizer and/or the bottom of the second deethanizer may be used as the primary absorbent, and a portion of the mixed C4+ fraction derived from the bottom of the depropanizer may be used as the secondary absorbent; or both the primary absorbent and the secondary absorbent may be the mixed C4+ fraction derived from the bottom of the depropanizer; or both the primary absorbent and the secondary absorbent may be the mixed C4 fraction derived from the bottom of the second deethanizer and the top of the debutanizer.

Based on the technical solution of the process of the present invention and various embodiments thereof, it can be known that the process of the present invention can be easily incorporated into the prior art without too much changes or modifications to the old separation schemes. Thus, the process of the present invention can be used in the prior art to reach the corresponding technical improvements very well.

BRIEF DESCRIPTION OF THE DRAWINGS

Now, the demethanizer and several typical embodiments of the process of the present invention are further illustrated with reference to the drawings, herein all the embodiments are not intended to limit the scope of the present invention.

In the drawings.

DETAILED DESCRIPTION OF THE INVENTION

Now, several typical embodiments of the process of the present invention are further illustrated in details with reference to the drawings.

Figure 1:
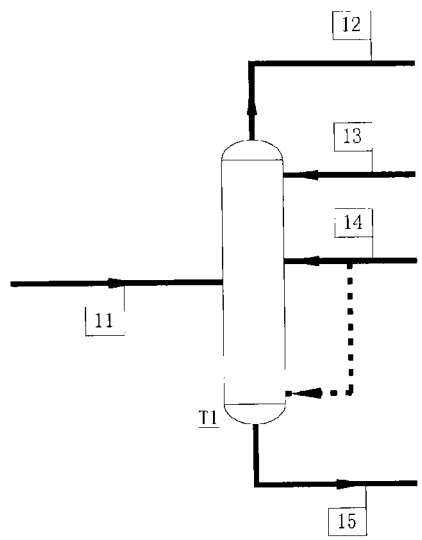
FIG. 1 is a schematic representative of the demethanizer in the process of the present invention.

Firstly, the demethanizer in the process of the present invention is described with reference to FIG. 1. In FIG. 1 the depicted is a schematic representative of demethanizer T1 in the process of the present invention, wherein into the demethanizer feedstock 11 is introduced at the middle, primary absorbent 14 is introduced at the middle or at both the middle and the bottom proportionally (as shown by the dotted line), secondary absorbent 13 is introduced at the top, and then top fraction 12 primarily comprising hydrogen and methane and bottom fraction 15 primarily comprising the absorbents and C2+ fraction are obtained. Now, the cases wherein the pyrolysis gas from preparation of lower carbon olefins is separated in a sequential scheme are described with reference to FIG. 2 and FIG. 3.

Figure 2:
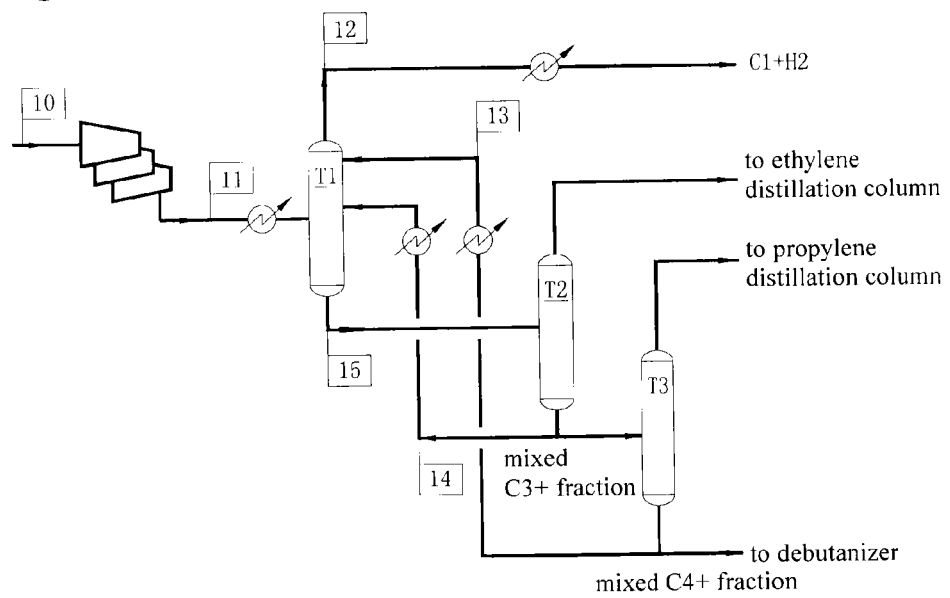
FIG. 2 is an embodiment of the process of the present invention, wherein the pyrolysis gas is separated in a sequential scheme, wherein the pyrolysis gas is compressed and fed into the demethanizer, wherein the primary absorbent is the mixed C3+ fraction from the bottom of the deethanizer, and the secondary absorbent is the mixed C4+ fraction from the bottom of the depropanizer.

Referring to the scheme shown in FIG. 2, pyrolysis gas 10 from preparation of lower carbon olefins is compressed and introduced as feedstock 11 into demethanizer T1, primary absorbent 14 is the mixed C3+ fraction from the bottom of deethanizer T2, which is cooled and introduced into the middle of demethanizer T1, and secondary absorbent 13 is the mixed C4+ fraction from the bottom of depropanizer T3, which is cooled and introduced into the top of demethanizer T1; the primary absorbent and the secondary absorbent together absorb C2+ fraction from feedstock 11 in demethanizer T1 to obtain top fraction 12 primarily comprising methane and hydrogen, which is used as fuel gas after the cooling capacity being recovered therefrom, and bottom fraction 15 primarily comprising the absorbents and C2+ fraction, which is introduced into deethanizer T2; from deethanizer T2 the top fraction is introduced into the ethylene distillation column and the bottom fraction is introduced into depropanizer T3; from the depropanizer T3 the top fraction is introduced into the propylene distillation column and the remaining portion of the bottom fraction is introduced into the debutanizer.

Figure 3:
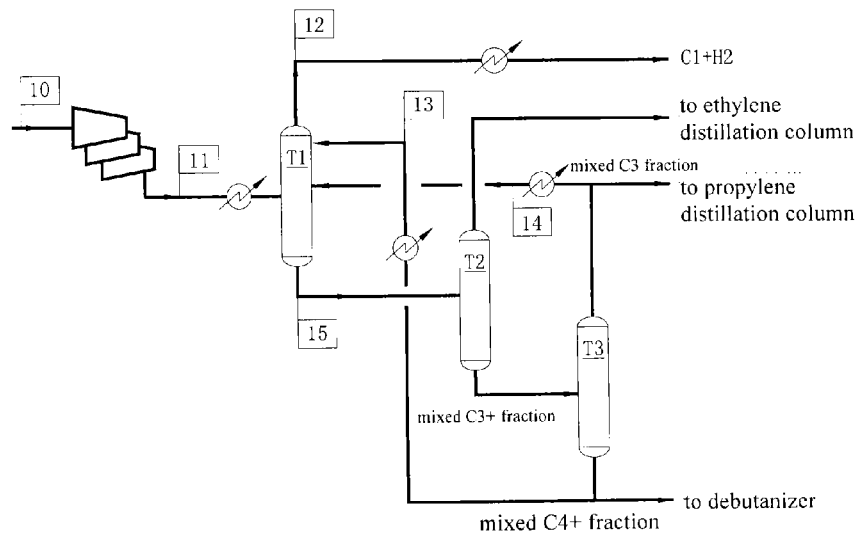
FIG. 3 is another embodiment of the process of the present invention, wherein the pyrolysis gas is separated in a sequential scheme, wherein the pyrolysis gas is compressed and fed into the demethanizer, wherein the primary absorbent is the mixed C3 fraction from the top of the depropanizer, and the secondary absorbent is the mixed C4+ fraction from the bottom of the depropanizer.

And, referring to the scheme shown in FIG. 3, pyrolysis gas 10 from preparation of lower carbon olefins is compressed and introduced as feedstock 11 into demethanizer T1, primary absorbent 14 is the mixed C3 fraction from the top of depropanizer T3, which is cooled and introduced into the middle of demethanizer T1, and secondary absorbent 13 is the mixed C4+ fraction from the bottom of depropanizer T3, which is cooled and introduced into the top of demethanizer T1; the primary absorbent and the secondary absorbent together absorb C2+ fraction from feedstock 11 in demethanizer T1 to obtain top fraction 12 primarily comprising methane and hydrogen, which is used as fuel gas after the cooling capacity being recovered therefrom, and bottom fraction 15 primarily comprising the absorbents and C2+ fraction, which is introduced into deethanizer T2; from deethanizer T2 the top fraction is introduced into the ethylene distillation column and the bottom fraction is introduced into depropanizer T3; from depropanizer T3 the remaining portion of the top fraction is introduced into the propylene distillation column and the remaining portion of the bottom fraction is introduced into the debutanizer.

Furthermore, the cases wherein the pyrolysis gas from preparation of lower carbon olefins is separated in a front end depropanizer scheme are described with reference to FIG. 4.

Figure 4:
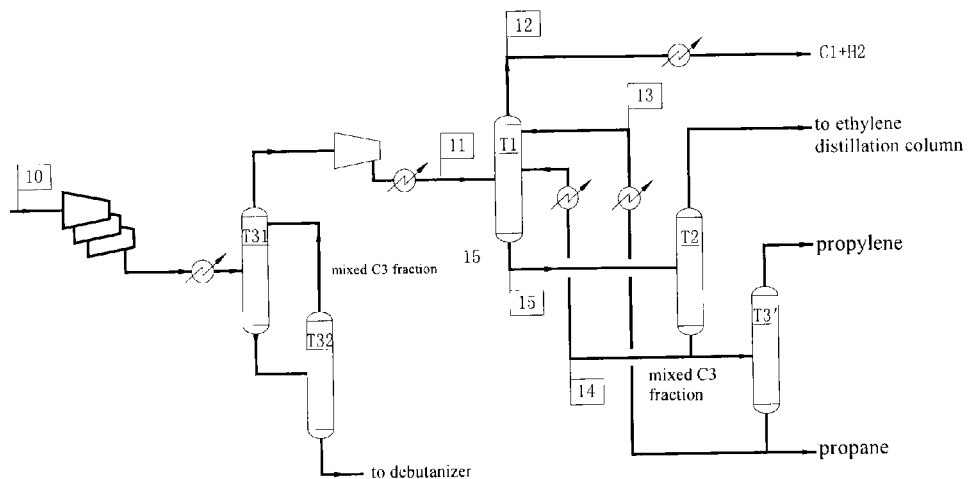
FIG. 4 is another embodiment of the process of the present invention, wherein the pyrolysis gas is separated in a front end depropanizer scheme, wherein a high pressure depropanizer and a low pressure depropanizer is used in combination, and the pyrolysis gas is compressed and fed into the high pressure depropanizer, from which the top fraction is compressed and fed into the demethanizer, wherein the primary absorbent is the mixed C3 fraction from the bottom of the deethanizer, and the secondary absorbent is the C3 alkane fraction from the bottom of the propylene distillation column.

Referring to the scheme shown in FIG. 4, pyrolysis gas 10 from preparation of lower carbon olefins is compressed and introduced into high pressure depropanizer T31 to be split to obtain a top fraction primarily comprising C3 and the lower fractions, which is compressed and introduced as feedstock 11 into demethanizer T1, and a bottom fraction, which is introduced into low pressure depropanizer T32 to be split furthermore; from low pressure depropanizer T32 the top fraction i.e. the mixed C3 fraction is back to the top of high pressure depropanizer T31 and the bottom fraction is introduced into the debutanizer; primary absorbent 14 is the bottom fraction, i.e. the mixed C3 fraction from deethanizer T2, which is compressed and introduced into the middle of demethanizer T1, and secondary absorbent 13 is the C3 alkane fraction, i.e. propane fraction from the bottom of propylene distillation column T3', which is cooled and introduced into the top of demethanizer T1; the primary absorbent and the secondary absorbent together absorb C2+ fraction from feedstock 11 in demethanizer T1 to obtain top fraction 12 primarily comprising methane and hydrogen, which is used as fuel gas after the cooling capacity being recovered therefrom, and bottom fraction 15 primarily comprising the absorbents and C2+ fraction, which is introduced into deethanizer T2; from deethanizer T2 the top fraction is introduced into the ethylene distillation column and the bottom fraction is introduced into propylene distillation column T3'; from propylene distillation column T3' the top fraction, i.e. propylene fraction is withdrawn from the scheme as product and the bottom fraction, i.e. the remaining portion of the propane fraction is withdrawn from the scheme as byproduct.

Furthermore, the cases wherein the pyrolysis gas from preparation of lower carbon olefins is separated in a front end deethanizer scheme are described with reference to FIG. 5 and FIG. 6.

Figure 5:
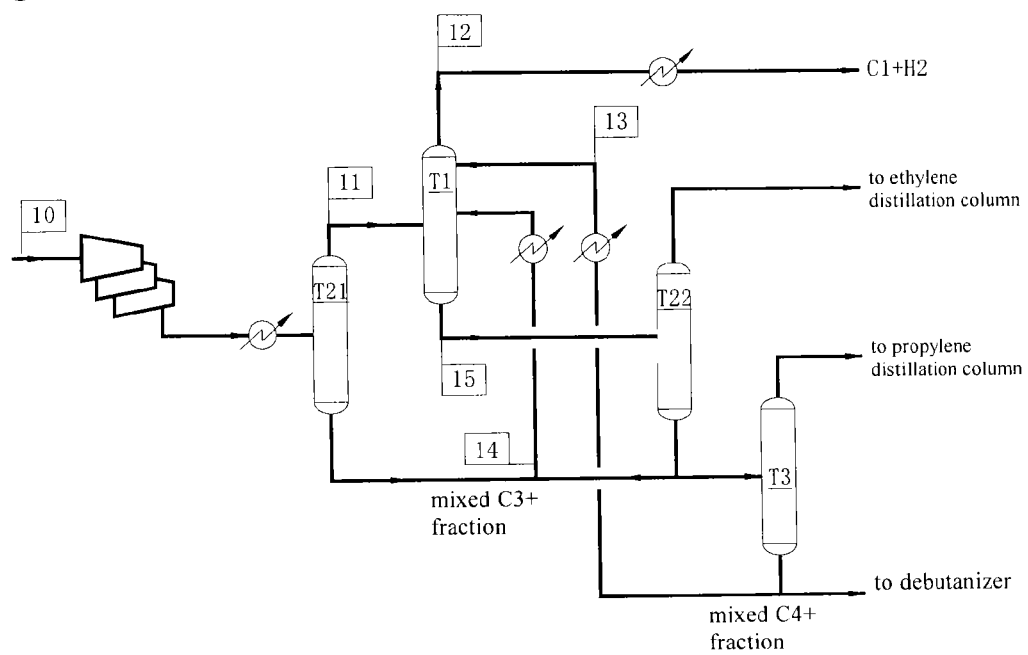
FIG. 5 is another embodiment of the process of the present invention, wherein the pyrolysis gas is separated in a front end deethanizer scheme comprising a first deethanizer and a second deethanizer, wherein the pyrolysis gas is compressed and fed into the first deethanizer, from which the top fraction is fed into the demethanizer, from which the bottom fraction is fed into the second deethanizer, wherein the primary absorbent is the mixed C3+ fraction from the bottom of the first deethanizer and the bottom of the second deethanizer, and the secondary absorbent is the mixed C4+ fraction from the bottom of the depropanizer.

Referring to the scheme shown in FIG. 5, pyrolysis gas 10 from preparation of lower carbon olefins is compressed and introduced into first deethanizer T21, from which the top fraction is introduced as feedstock 11 into demethanizer T1; primary absorbent 14 is the mixed C3+ fraction derived from the bottom of first deethanizer T21 and the bottom of second deethanizer T22, which is cooled and introduced into the middle of demethanizer T1, and secondary absorbent 13 is the mixed C4+ fraction from the bottom of depropanizer T3, which is cooled and introduced into the top of demethanizer T1; the primary absorbent and the secondary absorbent together absorb C2 fraction from feedstock 11 in demethanizer T1 to obtain top fraction 12 primarily comprising methane and hydrogen, which is used as fuel gas after the cooling capacity being recovered therefrom, and bottom fraction 15 primarily comprising the absorbents and C2 fraction, which is introduced into second deethanizer T22; from second deethanizer T22 the top fraction is introduced into the ethylene distillation column; the remaining portion of the bottom fraction from first deethanizer T21 and the remaining portion of the bottom fraction from second deethanizer T22 are introduced into depropanizer T3; from depropanizer T3 the top fraction is introduced into the propylene distillation column and the remaining portion of the bottom fraction is introduced into the debutanizer.

Figure 6:
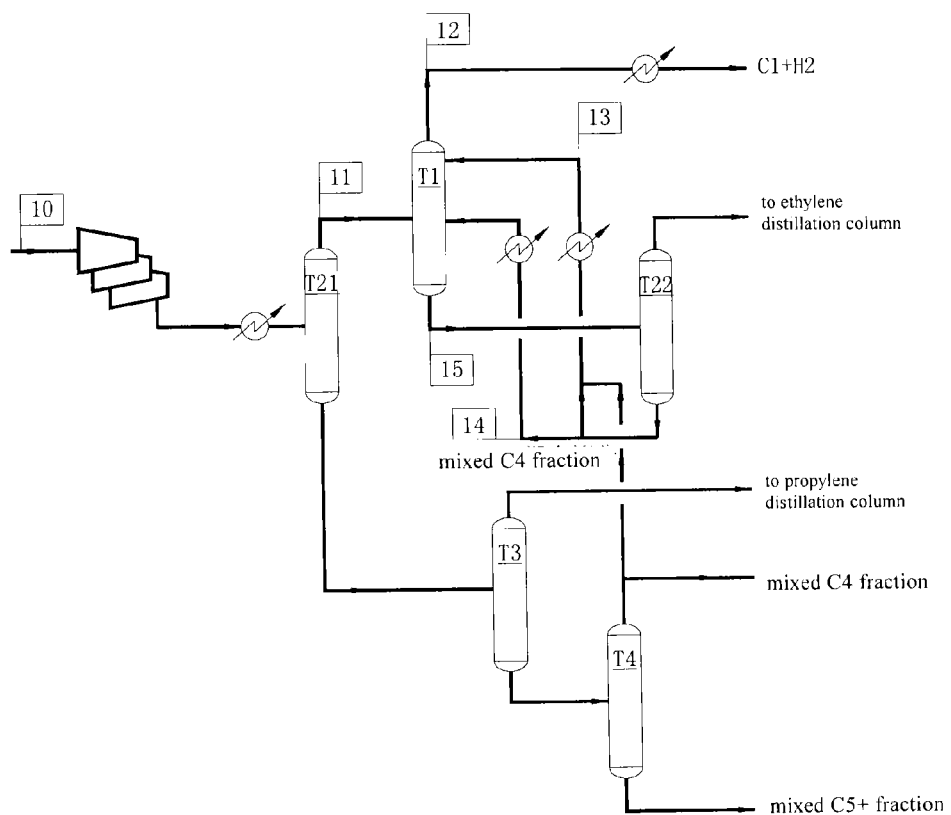
FIG. 6 is another embodiment of the process of the present invention, wherein the pyrolysis gas is separated in a front end deethanizer scheme comprising a first deethanizer and a second deethanizer, wherein the pyrolysis gas is compressed and fed into the first deethanizer, from which the top fraction is fed into the demethanizer, from which the bottom fraction is fed into the second deethanizer, wherein both the primary absorbent and the secondary absorbent are the mixed C4 fraction derived from the bottom of the second deethanizer and the top of the debutanizer, and wherein the mixed C4 fraction derived from the top of the debutanizer is introduced into the line for the secondary absorbent.

And, referring to the scheme shown in FIG. 6, pyrolysis gas 10 from preparation of lower carbon olefins is compressed and introduced into first deethanizer T21, from which the top fraction is introduced as feedstock 11 into demethanizer T1 and the bottom fraction is introduced into depropanizer T3 to be further split; both primary absorbent 14 and secondary absorbent 13 are the mixed C4 fraction, which is derived from the bottom of the second deethanizer and the top of the debutanizer, and introduced into the middle and the top of demethanizer T1 after being cooled respectively, wherein the mixed C4 fraction from the top of the debutanizer is introduced into the line for the secondary absorbent to the top of demethanizer T1; the primary absorbent and the secondary absorbent together absorb C2 fraction from feedstock 11 in demethanizer T1 to obtain top fraction 12 primarily comprising methane and hydrogen, which is used as fuel gas after the cooling capacity being recovered therefrom, and bottom fraction 15 primarily comprising the absorbents and C2 fraction, which is introduced into second deethanizer T22; from second deethanizer T22 the top fraction is introduced into the ethylene distillation column; from depropanizer T3 the top fraction is introduced into the propylene distillation column and the bottom fraction is introduced into the debutanizer; from the debutanizer the bottom fraction is introduced into the subsequent process or withdrawn from the scheme as byproduct. Furthermore, in addition to being used as the primary and secondary absorbents, the remaining portion of the bottom fraction of second deethanizer T22 and the remaining portion of the top fraction of debutanizer T4 are introduced into the subsequent process or withdrawn from the scheme as byproducts.

Now, the present invention is further illustrated by the following examples, which are not intended to limit the scope of the present invention.

EXAMPLES

Example 1

This example is provided regarding the cases wherein the pyrolysis gas from preparation of lower carbon olefins is separated in the sequential scheme as shown in FIG. 2. The operation parameters for effecting the process are listed in Table 1, and the calculated results are shown in Table 2.

TABLE 1

The operation parameters for the demethanizer in example 1

| Item | Unit | Value |
| --- | --- | --- |
| Feed pressure of demethanizer | MPaG | 3.1 |
| Top pressure of demethanizer T1 | MPaG | 2.6 |
| Temperature of demethanizer T1 (Top/Bottom) | ☐ | 6/23 |

TABLE 2

The results of the simulation calculation for the scheme in example1

| | Stream No. | | | | | |
|---|---|---|---|---|---|---|
| | 10 | 11 | 12 | 13 | 14 | 15 |
| Temperature | 40 | 32 | −32.6 | −10 | 75.8 | 22.7 |
| Pressure MPaG | 0.03 | 3.13 | 2.615 | 2.955 | 2.763 | 2.665 |
| Flowrate kg/hr | 54141.52 | 52061.597 | 855.981 | 3570.752 | 14194.084 | 68970.451 |
| Molar composition | | | | | | |
| H2O | 0.020744 | 0.019697 | 0.398293 | 0.000000 | 0.000000 | 0.000000 |
| CH4 | 0.025334 | 0.027118 | 0.548258 | 0.000000 | 0.000000 | 0.000003 |
| C2H4 | 0.470997 | 0.502521 | 0.004823 | 0.000000 | 0.000024 | 0.420781 |
| C2H6 | 0.010853 | 0.013129 | 0.000172 | 0.000000 | 0.000357 | 0.011052 |
| C3H6 | 0.310396 | 0.331159 | 0.008995 | 0.005102 | 0.696495 | 0.395935 |
| C3H8 | 0.024604 | 0.027332 | 0.000694 | 0.001811 | 0.057643 | 0.032754 |
| 1,3-C4H6 | 0.000730 | 0.000781 | 0.000186 | 0.010065 | 0.002468 | 0.001402 |
| C4H8 | 0.053305 | 0.056948 | 0.010925 | 0.726583 | 0.179559 | 0.102019 |
| i-C4H10 | 0.000076 | 0.000082 | 0.000030 | 0.001009 | 0.000253 | 0.000144 |
| n-C4H10 | 0.002353 | 0.002519 | 0.000459 | 0.032268 | 0.007955 | 0.004520 |
| C5 | 0.011768 | 0.011766 | 0.000486 | 0.152975 | 0.037523 | 0.021319 |
| C6 | 0.005211 | 0.005577 | 0.000004 | 0.069310 | 0.017542 | 0.009967 |
| CO | 0.000395 | 0.000414 | 0.008368 | 0.000000 | 0.000000 | 0.000000 |
| CO2 | 0.000199 | 0.000000 | 0.000000 | 0.000000 | 0.000000 | 0.000000 |
| CH4O | 0.002438 | 0.000002 | 0.000000 | 0.000031 | 0.000007 | 0.000004 |
| C2H6O | 0.002486 | 0.000051 | 0.000009 | 0.000137 | 0.000117 | 0.000067 |
| H2O | 0.057250 | 0.000000 | 0.000000 | 0.000000 | 0.000000 | 0.000000 |
| O2 | 0.000002 | 0.000000 | 0.000000 | 0.000000 | 0.000000 | 0.000000 |
| N2 | 0.000859 | 0.000905 | 0.018291 | 0.000000 | 0.000000 | 0.000000 |

As known from the results shown in Table 2, when the process of the present invention is effected according to the scheme shown in FIG. 2, at the overhead of the absorption column the ethylene concentration is of 0.48% and the propylene concentration is of 0.9%, that is to say, relative to the ethylene and propylene in the fed pyrolysis gas, at the top of the demethanizer the loss rates for ethylene and propylene are of 0.05% and 0.13% respectively. Thus, when being effected according to the scheme shown in FIG. 2, the process of the present invention reaches excellent technical effects.

Example 2

This example is provided regarding the cases wherein the pyrolysis gas from preparation of lower carbon olefins is separated in the sequential scheme as shown in FIG. 3. The operation parameters for effecting the process are listed in Table 3, and the calculated results are shown in Table 4.

TABLE 3

The operation parameters for the demethanizer in example 2

| Item | Unit | Value |
|---|---|---|
| Feed pressure of demethanizer | MPaG | 3.1 |
| Top pressure of demethanizer T1 | MPaG | 2.6 |
| Temperature of demethanizer T1 (Top/Bottom) | | −2/21 |

TABLE 4

The results of the simulation calculation for the scheme in example 2

| | Stream No. | | | | | |
|---|---|---|---|---|---|---|
| | 10 | 11 | 12 | 13 | 14 | 15 |
| Temperature | 40 | 32 | −28.6 | −10 | 40 | 21.3 |
| Pressure MPaG | 0.03 | 3.13 | 2.615 | 2.955 | 2.89 | 2.665 |
| Flowrate kg/hr | 54141.52 | 52061.597 | 845.931 | 5578.453 | 9680.951 | 66475.069 |
| Molar composition | | | | | | |
| H2O | 0.020744 | 0.019697 | 0.400332 | 0.000000 | 0.000000 | 0.000000 |
| CH4 | 0.025334 | 0.027118 | 0.551066 | 0.000000 | 0.000000 | 0.000004 |
| C2H4 | 0.470997 | 0.502521 | 0.002856 | 0.000000 | 0.000024 | 0.43082 |
| C2H6 | 0.010853 | 0.013129 | 0.000085 | 0.000000 | 0.000048 | 0.011319 |
| C3H6 | 0.310396 | 0.331159 | 0.002943 | 0.005099 | 0.923094 | 0.405547 |
| C3H8 | 0.024604 | 0.027332 | 0.000384 | 0.001814 | 0.075913 | 0.033504 |
| 1,3-C4H6 | 0.00073 | 0.000781 | 0.00023 | 0.009919 | 0.000011 | 0.001188 |
| C4H8 | 0.053305 | 0.056948 | 0.013961 | 0.726351 | 0.00036 | 0.086871 |
| i-C4H10 | 0.000076 | 0.000082 | 0.000036 | 0.001015 | 0.000005 | 0.000123 |
| n-C4H10 | 0.002353 | 0.002519 | 0.000599 | 0.032215 | 0.000001 | 0.003846 |
| C5 | 0.011768 | 0.011766 | 0.000694 | 0.151471 | 0.000000 | 0.018106 |
| C6 | 0.005211 | 0.005577 | 0.000008 | 0.071954 | 0.000000 | 0.008604 |
| CO | 0.000395 | 0.000414 | 0.008411 | 0.000000 | 0.000000 | 0.000000 |
| CO2 | 0.000199 | 0.000000 | 0.000000 | 0.000000 | 0.000000 | 0.000000 |

TABLE 4-continued

The results of the simulation calculation for the scheme in example 2

| | Stream No. | | | | | |
|---|---|---|---|---|---|---|
| | 10 | 11 | 12 | 13 | 14 | 15 |
| CH4O | 0.002438 | 0.000002 | 0.000000 | 0.00003 | 0.000000 | 0.000004 |
| C2H6O | 0.002486 | 0.000051 | 0.00001 | 0.00013 | 0.000111 | 0.000065 |
| H2O | 0.05725 | 0.000000 | 0.000000 | 0.000000 | 0.000000 | 0.000000 |
| O2 | 0.000002 | 0.000000 | 0.000000 | 0.000000 | 0.000000 | 0.000000 |
| N2 | 0.000859 | 0.000905 | 0.018385 | 0.000000 | 0.000000 | 0.000000 |

As known from the results shown in Table 4, when the process of the present invention is effected according to the scheme shown in FIG. 3, at the overhead of the absorption column the ethylene concentration is of 0.29% and the propylene concentration is of 0.29%, that is to say, relative to the ethylene and propylene in the fed pyrolysis gas, at the top of the demethanizer the loss rates for ethylene and propylene are of 0.03% and 0.04% respectively. Thus, when being effected according to the scheme shown in FIG. 3, the process of the present invention also reaches excellent technical effects.

TABLE 5

The operation parameters for the demethanizer in example 3

| Item | Unit | Value |
|---|---|---|
| Feed pressure of demethanizer | MPaG | 3.1 |
| Top pressure of demethanizer T1 | MPaG | 2.6 |
| Temperature of demethanizer T1 (Top/Bottom) | ? | −10/19 |

TABLE 6

The results of the simulation calculation for the scheme in example 3

| | Stream No. | | | | | |
|---|---|---|---|---|---|---|
| | 10 | 11 | 12 | 13 | 14 | 15 |
| Temperature | 40 | 55.5 | −24 | −21 | 62.8 | 19.2 |
| Pressure MPaG | 0.03 | 3.13 | 2.615 | 2.955 | 2.763 | 2.665 |
| Flowrate kg/hr | 54141.52 | 45043.202 | 1142.131 | 4418.281 | 14351.4 | 62671.357 |
| Molar composition | | | | | | |
| H2O | 0.020744 | 0.021363 | 0.365577 | 0.000000 | 0.000000 | 0.000000 |
| CH4 | 0.025334 | 0.029409 | 0.503202 | 0.000000 | 0.000000 | 0.000004 |
| C2H4 | 0.470997 | 0.544987 | 0.000143 | 0.000000 | 0.000037 | 0.432746 |
| C2H6 | 0.010853 | 0.014239 | 0.000034 | 0.000000 | 0.000363 | 0.011375 |
| C3H6 | 0.310396 | 0.358828 | 0.008758 | 0.052366 | 0.795238 | 0.442266 |
| C3H8 | 0.024604 | 0.029473 | 0.097473 | 0.937192 | 0.202141 | 0.112374 |
| 1,3-C4H6 | 0.00073 | 0.000006 | 0.000002 | 0.000123 | 0.000033 | 0.000018 |
| C4H8 | 0.053305 | 0.000221 | 0.000063 | 0.004479 | 0.001193 | 0.000662 |
| i-C4H10 | 0.000076 | 0.000004 | 0.000001 | 0.000067 | 0.00002 | 0.000011 |
| n-C4H10 | 0.002353 | 0.000003 | 0.000000 | 0.000036 | 0.000011 | 0.000006 |
| C5 | 0.011768 | 0.000000 | 0.000000 | 0.000000 | 0.000000 | 0.000000 |
| C6 | 0.005211 | 0.000000 | 0.000000 | 0.000000 | 0.000000 | 0.000000 |
| CO | 0.000395 | 0.000449 | 0.00768 | 0.000000 | 0.000000 | 0.000000 |
| CO2 | 0.000199 | 0.000000 | 0.000000 | 0.000000 | 0.000000 | 0.000000 |
| CH4O | 0.002438 | 0.000000 | 0.000000 | 0.000000 | 0.000000 | 0.000000 |
| C2H6O | 0.002486 | 0.000038 | 0.000243 | 0.005009 | 0.000854 | 0.000475 |
| H2O | 0.05725 | 0.000000 | 0.000000 | 0.000000 | 0.000000 | 0.000000 |
| O2 | 0.000002 | 0.000000 | 0.000000 | 0.000000 | 0.000000 | 0.000000 |
| N2 | 0.000859 | 0.000981 | 0.016788 | 0.000000 | 0.000000 | 0.000000 |

Example 3

This example is provided regarding the cases wherein the pyrolysis gas from preparation of lower carbon olefins is separated in the front end depropanizer scheme as shown in FIG. 4. The operation parameters for effecting the process are listed in Table 5, and the calculated results are shown in Table 6.

As known from the results shown in Table 6, when the process of the present invention is effected according to the scheme shown in FIG. 4, at the overhead of the absorption column the ethylene concentration is of 0.01% and the propylene concentration is of 0.87%, that is to say, relative to the ethylene and propylene in the fed pyrolysis gas, at the top of the demethanizer the loss rates for ethylene and propylene are of 0.002% and 0.14% respectively. Thus, when being effected according to the scheme shown in FIG. 4, the process of the present invention also reaches excellent technical effects.

Example 4

This example is provided regarding the cases wherein the pyrolysis gas from preparation of lower carbon olefins is separated in the front end deethanizer scheme as shown in FIG. 5. The operation parameters for effecting the process are listed in Table 7, and the calculated results are shown in Table 8.

TABLE 7

The operation parameters for the demethanizer in example 4

| Item | Unit | Value |
|---|---|---|
| Feed pressure of demethanizer | MPaG | 3.1 |
| Top pressure of demethanizer T1 | MPaG | 2.6 |
| Temperature of demethanizer T1 (Top/Bottom) | ? | −5/18 |

TABLE 8

The results of the simulation calculation for the scheme in example 4

| | Stream No. | | | | | |
|---|---|---|---|---|---|---|
| | 10 | 11 | 12 | 13 | 14 | 15 |
| Temperature? | 40 | 32 | −18.5 | −10 | 83.4 | 18.3 |
| Pressure MPaG | 0.03 | 3.13 | 2.615 | 2.955 | 2.763 | 2.665 |
| Flowrate kg/hr | 54141.52 | 52061.597 | 879.41 | 15127.658 | 24047.438 | 60718.006 |
| Molar composition | | | | | | |
| H2O | 0.020744 | 0.019697 | 0.397212 | 0.000000 | 0.000000 | 0.000000 |
| CH4 | 0.025334 | 0.027118 | 0.546013 | 0.000000 | 0.000000 | 0.000041 |
| C2H4 | 0.470997 | 0.502521 | 0.00481 | 0.000000 | 0.00006 | 0.49868 |
| C2H6 | 0.010853 | 0.013129 | 0.000012 | 0.000000 | 0.000521 | 0.012973 |
| C3H6 | 0.310396 | 0.331159 | 0.00109 | 0.005168 | 0.549859 | 0.178334 |
| C3H8 | 0.024604 | 0.027332 | 0.000298 | 0.001776 | 0.045771 | 0.015046 |
| 1,3-C4H6 | 0.00073 | 0.000781 | 0.000346 | 0.010129 | 0.004091 | 0.002994 |
| C4H8 | 0.053305 | 0.056948 | 0.021206 | 0.726629 | 0.29528 | 0.215564 |
| i-C4H10 | 0.000076 | 0.000082 | 0.000049 | 0.001007 | 0.000412 | 0.000299 |
| n-C4H10 | 0.002353 | 0.002519 | 0.000929 | 0.032264 | 0.013096 | 0.009567 |
| C5 | 0.011768 | 0.011766 | 0.001405 | 0.153648 | 0.062235 | 0.045668 |
| C6 | 0.005211 | 0.005577 | 0.000021 | 0.068416 | 0.028321 | 0.020561 |
| CO | 0.000395 | 0.000414 | 0.008345 | 0.000000 | 0.000000 | 0.000000 |
| CO2 | 0.000199 | 0.000000 | 0.000000 | 0.000000 | 0.000000 | 0.000000 |
| CH4O | 0.002438 | 0.000002 | 0.000000 | 0.000031 | 0.000012 | 0.000009 |
| C2H6O | 0.002486 | 0.000051 | 0.000009 | 0.000107 | 0.000113 | 0.000054 |
| H2O | 0.05725 | 0.000000 | 0.000000 | 0.000000 | 0.000000 | 0.000000 |
| O2 | 0.000002 | 0.000000 | 0.000000 | 0.000000 | 0.000000 | 0.000000 |
| N2 | 0.000859 | 0.000905 | 0.018242 | 0.000000 | 0.000000 | 0.000000 |

As known from the results shown in Table 8, when the process of the present invention is effected according to the scheme shown in FIG. 5, at the overhead of the absorption column the ethylene concentration is of 0.48% and the propylene concentration is of 0.11%, that is to say, relative to the ethylene and propylene in the fed pyrolysis gas, at the top of the demethanizer the loss rates for ethylene and propylene are of 0.05% and 0.02% respectively. Thus, when being effected according to the scheme shown in FIG. 5, the process of the present invention also reaches excellent technical effects.

Example 5

This example is provided regarding the cases wherein the pyrolysis gas from preparation of lower carbon olefins is separated in the front end deethanizer scheme as shown in FIG. 6. The operation parameters for effecting the process are listed in Table 9, and the calculated results are shown in Table 10.

TABLE 9

The operation parameters for the demethanizer in example 5

| Item | Unit | Value |
|---|---|---|
| Feed pressure of demethanizer | MPaG | 3.1 |
| Top pressure of demethanizer T1 | MPaG | 2.6 |
| Temperature of demethanizer T1 (Top/Bottom) | ? | −14/17 |

TABLE 10

The results of the simulation calculation for the scheme in example 5

| | Stream No. | | | | | |
|---|---|---|---|---|---|---|
| | 10 | 11 | 12 | 13 | 14 | 15 |
| Temperature? | 40 | 32 | −27.8 | −20 | 40 | 17.1 |
| Pressure MPaG | 0.03 | 3.13 | 2.615 | 2.955 | 2.743 | 2.665 |
| Flowrate kg/hr | 54141.52 | 52061.597 | 853.461 | 10181.999 | 24756.056 | 56506.913 |
| Molar composition | | | | | | |
| H2O | | 0.020744 | 0.019697 | 0.399288 | 0.000000 | 0.000000 | 0.000000 |
| CH4 | | 0.025334 | 0.027118 | 0.548868 | 0.000000 | 0.000000 | 0.000045 |

TABLE 10-continued

The results of the simulation calculation for the scheme in example 5

| | Stream No. | | | | | |
|---|---|---|---|---|---|---|
| | 10 | 11 | 12 | 13 | 14 | 15 |
| C2H4 | 0.470997 | 0.502521 | 0.005987 | 0.000016 | 0.000016 | 0.539403 |
| C2H6 | 0.010853 | 0.013129 | 0.000393 | 0.000594 | 0.000595 | 0.014098 |
| C3H6 | 0.310396 | 0.331159 | 0.000843 | 0.00575 | 0.005063 | 0.002501 |
| C3H8 | 0.024604 | 0.027332 | 0.000255 | 0.002087 | 0.001839 | 0.000843 |
| 1,3-C4H6 | 0.00073 | 0.000781 | 0.000268 | 0.012757 | 0.012754 | 0.005694 |
| C4H8 | 0.053305 | 0.056948 | 0.016573 | 0.931935 | 0.932823 | 0.416472 |
| i-C4H10 | 0.000076 | 0.000082 | 0.000041 | 0.001306 | 0.001301 | 0.000581 |
| n-C4H10 | 0.002353 | 0.002519 | 0.000727 | 0.041318 | 0.041351 | 0.018463 |
| C5 | 0.011768 | 0.011766 | 0.00002 | 0.004021 | 0.004044 | 0.001806 |
| C6 | 0.005211 | 0.005577 | 0.000000 | 0.000000 | 0.000000 | 0.000000 |
| CO | 0.000395 | 0.000414 | 0.008389 | 0.000000 | 0.000000 | 0.000000 |
| CO2 | 0.000199 | 0.000000 | 0.000000 | 0.000000 | 0.000000 | 0.000000 |
| CH4O | 0.002438 | 0.000002 | 0.000000 | 0.000038 | 0.000038 | 0.000017 |
| C2H6O | 0.002486 | 0.000051 | 0.00001 | 0.000178 | 0.000175 | 0.000078 |
| H2O | 0.05725 | 0.000000 | 0.000000 | 0.000000 | 0.000000 | 0.000000 |
| O2 | 0.000002 | 0.000000 | 0.000000 | 0.000000 | 0.000000 | 0.000000 |
| N2 | 0.000859 | 0.000905 | 0.018337 | 0.000000 | 0.000000 | 0.000000 |

As known from the results shown in Table 10, when the process of the present invention is effected according to the scheme shown in FIG. 6, at the overhead of the absorption column the ethylene concentration is of 0.60% and the propylene concentration is of 0.08%, that is to say, relative to the ethylene and propylene in the fed pyrolysis gas, at the top of the demethanizer the loss rates for ethylene and propylene are of 0.06% and 0.013% respectively. Thus, when being effected according to the scheme shown in FIG. 6, the process of the present invention also reaches excellent technical effects.

The invention claimed is:

1. A process for separating by absorption a pyrolysis gas from a preparation of lower carbon olefins, the process comprising introducing a primary absorbent and a secondary absorbent into a demethanizer and separating by absorption a feedstock of the demethanize through countercurrent contact at a moderate temperature and pressure, wherein the feedstock is introduced at the middle or the bottom of the demethanizer, the primary absorbent is introduced at the middle of the demethanizer only, or at the middle and at the bottom of the demethanizer simultaneously, the second absorbent is introduced at the top of the demethanizer, and wherein the primary absorbent and the secondary absorbent are introduced into the demethanizer at a total mass flowrate ratio of the primary absorbent to the secondary absorbent of 10-1.05, thereby obtain top fraction primarily comprising hydrogen and methane and a bottom fraction primarily comprising the primary and secondary absorbents and a C2+ fraction,
wherein:
the primary absorbent essentially is a mixed Cn or Cn+ fraction;
the secondary absorbent essentially is a Cn' alkane fraction or mixed Cn' or Cn'+fraction; and
n and n' are independently 3, 4 or 5,
with the proviso that when the secondary absorbent is a mixed fraction, n' is not 3.

2. The process of claim 1, wherein in the demethanizer the temperature is above −45°C. and the pressure is from 1.5 to 3.5 MPaG.

3. The process of claim 2, wherein the primary absorbent is introduced into the demethanizer at the middle and the bottom simultaneously and a mass flowrate ration of the mass flowrate of the primary absorbent introduced at the middle of the demethanizer to the mass flowrate of the primary absorbent introduced at the bottom of the demethanizer is from 1.0 to 1.5.

4. The process of claim 1, wherein the primary absorbent and the feedstock are introduced into the demethanizer at a total mass flowrate ratio of the primary absorbent to the feedstock of from 0.03 to 4, and the primary absorbent and the secondary absorbent are introduced into the demethanizer at a total flowrate ratio of the primary absorbent to the secondary absorbent of from 10 to 1.05.

5. The process of claim 1, wherein the pyrolysis gas is sequentially separated and the pyrolysis gas is compressed and optionally finished and fed into the demethanizer, wherein in addition to the demethanizer, the process further comprises using a compressor, a finishing system, a deethanizer, a depropanizer, a debutanizer, an ethylene distillation column, and propylene distillation column.

6. The process of claim 5, wherein a portion of a mixed C3 fraction derived from the top of the depropanizer is the primary absorbent, and a portion of a C3 alkane fraction derived from the bottom of the propylene distillation column the secondary absorbent.

7. The process of claim 5, wherein a portion of a mixed C3 fraction derived from the top of the depropanizer is the primary absorbent, and a portion of a mixed C4+ fraction derived from the bottom of the depropanizer is the secondary absorbent.

8. The process of claim 5, wherein a portion of a mixed C3+ fraction derived from the bottom of the deethanizer is the primary absorbent, and a portion of a mixed C4+ fraction derived from the bottom of the depropanizer is the secondary absorbent.

9. The process of claim 5, wherein a portion of a mixed C3 fraction derived from the bottom of the deethanizer is the primary absorbent, and a portion of a mixed C4 fraction derived from the top of the debutanizer is the secondary absorbent.

10. The process of claim 5, wherein a portion of a mixed C4+ fraction derived at the bottom of the depropanizer is the primary absorbent, and a portion of a mixed C4 fraction derived from the top of the debutanizer is the secondary absorbent.

11. The process of claim 1, wherein the pyrolysis gas is separated in a front end depropanizer, wherein in addition to the demethanizer, the process further comprises using a compressor, a finishing system, a deethanizer, a depropanizer, a debutanizer, an ethylene distillation column, and a propylene distillation column.

12. The process of claim 11, wherein the front end depropanizer is a single depropanizer, the pyrolysis gas is compressed and then introduced into the depropanizer, from which the top fraction is optionally finished and then fed into the demethanizer and the bottom fraction is fed into the debutanizer, wherein a portion of a mixed C3 fraction derived from the bottom of the deethanize is the primary absorbent, and a portion of a C3 alkane fraction derived from the bottom of the propylene distillation column is the secondary absorbent.

13. The process of claim 11, wherein the front end depropanizer comprises a high pressure depropanizer and a low pressure depropanizer in combination, wherein the pyrolysis gas is compressed and then fed into the high pressure depropanizer, from which the top fraction is optionally finished and then fed into the demethanizer and the bottom fraction is fed into the low pressure depropanizer.

14. The process of claim 13, wherein from the low pressure depropanizer the top fraction is fed back to the high pressure depropanizer and a bottom fraction is fed into a debutanizer, wherein a portion of a mixed C3 fraction derived from the bottom of a deethanizer is the primary absorbent, and a portion of a C3 alkane fraction derived from the bottom of a propylene distillation column is the secondary absorbent.

15. The process of claim 14, wherein a portion or the entire top fraction of the low pressure depropanizer is also the primary absorbent, and from the low pressure depropanizer the remaining portion of the top fraction, is fed back to the high pressure depropanizer and the bottom fraction is fed into the debutanizer.

16. The process of claim 1, wherein the pyrolysis is separated in a front end deethanizer, wherein in addition to the demethanizer, the process further comprises using a compressor, a finishing system, a deethanizer, a depropanizer, a debutanizer, an ethylene distillation column, and a propylene distillation column, and wherein the deethanizer comprises a first deethanizer and a second deethanizer, and the pyrolysis gas is compressed and optionally finished and then fed into the first deethanizer, from which a top fraction is fed into the demethanizer and the bottom fraction is fed into the depropanizer, and the bottom fraction of the demethanizer is fed into the second deethanizer.

17. The process of claim 16, wherein a portion of a mixed C3 fraction derived from the top of the depropanizer is the primary absorbent, and a portion of a C3 alkane fraction derived from the bottom of the propylene distillation column is the secondary absorbent.

18. The process of claim 16, wherein a portion of a mixed C3+ fraction derived from the bottom of the first deethanizer is the primary absorbent, and a portion of a mixed C4 fraction derived from the top of the debutanizer is the secondary absorbent.

19. The process of claim 16, wherein a portion of a mixed C3+ fraction derived from the bottom of the first deethanizer is the primary absorbent, and a portion of a mixed C4+ fraction derived from the bottom of the depropanizer is the secondary absorbent.

20. The process of claim 16, wherein both the primary absorbent and the secondary absorbent are a mixed C4+ fraction derived from the bottom of the depropanizer.

21. The process of claim 16, wherein both the primary absorbent and the secondary absorbent are a mixed C4 fraction derived from the bottom of the second deethanizer and the top of the debutanizer.

* * * * *